United States Patent [19]

Springer

[11] Patent Number: 5,359,120
[45] Date of Patent: Oct. 25, 1994

[54] IMPROVEMENTS RELATING TO THE PRODUCTION OF PRODRUGS

[75] Inventor: Caroline J. Springer, London, United Kingdom

[73] Assignee: Cancer Research Campaign Technology Limited, London, United Kingdom

[21] Appl. No.: 681,536

[22] PCT Filed: Sep. 5, 1989

[86] PCT No.: PCT/GB89/01042

§ 371 Date: May 6, 1991

§ 102(e) Date: May 6, 1991

[87] PCT Pub. No.: WO90/02729

PCT Pub. Date: Mar. 22, 1990

[30] Foreign Application Priority Data

Sep. 5, 1988 [GB] United Kingdom ............... 8820850.9

[51] Int. Cl.$^5$ .................. C07C 237/30; C07C 309/66; A61K 31/165; A61K 31/255

[52] U.S. Cl. ......................................... 560/10; 560/16; 560/9; 560/28; 560/30; 560/41; 560/44; 562/456; 562/458

[58] Field of Search ................. 560/10, 16, 41, 44, 560/9, 10, 28, 30; 562/456, 458

[56] References Cited

FOREIGN PATENT DOCUMENTS 750155 3/1953 United Kingdom ................ 562/456

OTHER PUBLICATIONS

S.-C. J. Fu et al., "Synthesis and biological activity of isomers of N-[Bis(2-chloroethyl)aminobenzoyl] glutamic acid", *Journal of Medicinal Chemistry*, vol. 7(6), pp 759-762, see table I (Nov. 1964).

S.-C. J. Fu et al., "Dipeptide nitrogen mustards of glycine and gamma-amino-butyric acid", *Journal of Medicinal Chemistry*, vol. 9(2), pp. 214-216, see table I (Mar. 1966).

V. Sunel et al., "Syntheses of anticancer substances. XXI. Synthesis of the diethyl ester of p-[di($\beta$-chloroethyl)amino]benzoyl-L-aspartic acid with potential anticancer action", *Chemical Abstracts*, vol. 92 (23), Jun. 9, 1980 (Columbus, Ohio, US), see p. 721 abstract No. 198735j, & Inst. Politeh. Iasi, Sect. 2: Chim. Ing. Chim. 1979, 25(1-2), 85-9.

V. Sunel et al., "New derivatives of N-(p-aminobenzoyl)-L-aspartic acid with potential antitumor effect", *Chemical Abstracts*, vol. 98(23), Jun. 6th, 1983 (Columbus, Ohio, US), see p. 702, abstract No. 198688v, & Rev. Chim. (Bucharest) 1982, 33(12), 1099-101.

Cecal et al., Journal of Radioanalytical Chemistry, vol. 78, No. 2 (1983), 247-253.

Fu et al., "Synthesis and Biological Activity of Isomers of Glutamic Acid", Journal of Medicinal Chemistry, vol. 7, No. 6 (1964) pp. 759-762.

*Primary Examiner*—Marianne M. Cintins
*Assistant Examiner*—Keith MacMillan
*Attorney, Agent, or Firm*—Spencer, Frank & Schneider

[57] ABSTRACT

The invention provides compounds of the formula XX: M-Ar-CONH-R, where Ar represents an aromatic ring system, R-NH is the residue of an $\alpha$-amino acid R-NH$_2$ or oligopeptide R-NH$_2$ and contains at least one carboxylic acid group in the form of a tertiary butyl ester and M represents a nitrogen mustard group of formula (a), where Y and L, which may be the same or different in a molecule, are leaving groups. The compounds are useful intermediates for the production of nitrogen mustard prodrugs.

9 Claims, No Drawings

IMPROVEMENTS RELATING TO THE PRODUCTION OF PRODRUGS

CROSS REFERENCE TO RELATED APPLICATION

This application is the national stage of international application PCT/GB 89/01042 filed Sep. 5th, 1989, and claims priority to British Application 8820850.9 filed Sep. 5th, 1988.

THIS INVENTION relates to pro-drugs and is particularly concerned with novel intermediates for the production of enzyme activatable pro-drugs.

Over the years, many cytotoxic compounds have been discovered which are of potential use in cancer chemotherapy. Nitrogen mustards form one important family of such cytotoxic compounds. The clinical use of cytotoxic compounds in general and nitrogen mustards in particular has been limited because of the poor selectivity in the cytotoxic effect between tumour cells and normal cells.

One approach to overcome this problem has involved the development of so-called pro-drugs which are derivatives of the cytotoxic drug, often a relatively simple derivative, whose cytotoxic properties are considerably reduced compared to those of the Parent drug. Numerous proposals have been made for the administration of such pro-drugs to patients under regimes whereby the pro-drug is only converted to the cytotoxic drug in the region of the intended site of action.

One particularly promising approach involves the conversion of the nitrogen mustard into a reaction product with an amino acid or oligopeptide to form a pro-drug which can be converted to the parent nitrogen mustard at the site of intended action under the influence of an enzyme. This approach can be put into practice by the utilization of an antibody/enzyme conjugate in association with a pro-drug. The antibody/enzyme conjugate is one formed from an antibody to tumour associated antigen and an enzyme that will convert the pro-drug to the cytotoxic drug. In clinical practice, the antibody/enzyme conjugate is first administered to the patient and is allowed to localise in the region of the tumour to be treated. The pro-drug is then administered to the patient so that conversion of the pro-drug to the cytotoxic drug is also localised in the region of the tumour to be treated under the influence of the localised enzyme. Such a system is described in our co-pending International Application PCT/GB88/00181 published as WO88/07378.

Specific pro-drugs that can be used in the above-mentioned International Application are those based upon benzoic acid nitrogen mustards. The cytotoxic benzoic acid nitrogen mustard is converted, in accordance with the procedures described in our above-mentioned International Application, into an amide by reaction with an alpha-amino acid, the preferred alpha-amino acid being glutamic acid. In this case, the glutamic acid is linked to the nitrogen mustard through an amide bond formed between the carboxy group of the benzoic acid nitrogen mustard and the alpha-amino group of the glutamic acid.

Other pro-drugs can be prepared based on benzoic acid nitrogen mustards where the carboxy group is converted into a derivative with an oligopeptide or other protecting group which is removed in vivo, under the influence of an enzyme localised in the region of the tumour to be treated.

Pro-drugs of the type described in our above-mentioned Application and other pro-drugs embodying the same principle are administered as pro-drugs where the carboxy groups present in the glutamic acid or analogous residue, for example of aspartic acid, are in free carboxylic acid form. These pro-drugs are prepared by synthetic methods in which the carboxy groups present in the glutamic acid or analogous reactant are protected, normally in the form of an ethylester. Once the pro-drug has been prepared in the form of the ethoxy carbonyl compound, the carboxy protecting groups are removed to release the free carboxylic acid groups. In the synthetic methods described in our above-mentioned International Application, the protecting ethyl ester groups are removed by the conventional method of alkaline hydrolysis with aqueous sodium hydroxide followed by conversion of the resulting sodium salts into the free carboxylic diacid using hydrochloric acid. While this alkaline hydrolysis method is perfectly satisfactory for conversion of the ethyl ester into the free carboxylic acid, it has the serious practical disadvantage that the reaction conditions used to convert the ethyl ester to the carboxylic acid also adversely affects the nitrogen mustard part of the molecule causing degradation and consequently, loss of yield of the pro-drug.

We have now found an improved synthetic method based upon the utilization of a tertiary butyl ester to protect the free carboxy groups in the glutamic acid or analogous reagent, for example aspartic acid, during the synthesis of the pro-drug. According to our invention, we have found that the synthesis of the desired pro-drug proceeds satisfactorily utilising reagents containing a tertiary butyl ester grouping and that the tertiary butyl ester can be converted into the free carboxylic acid by treatment with an acid, for example in a non-aqueous medium. Trifluoroacetic acid and formic acid are examples of reagents which may be used to remove the carboxy protecting groups and which cause no adverse affect to the nitrogen mustard part of the molecule.

Accordingly, the present invention provides nitrogen mustard compounds of the formula XX:

where Ar represents an aromatic ring system, R-NH is the residue of an α-amino acid R-NH$_2$ or oligopeptide R-NH$_2$ containing at least one carboxylic acid group in the form of a tertiary butyl ester and M represents a nitrogen mustard group of formula

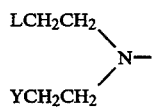

where Y and L, which may be the same or different in a molecule, are leaving groups, for example halogen (e.g. chlorine), mesyloxy, trifluoromesyloxy or 4-tosyloxy. The amide linkage of this compound is susceptible to enzymatic cleavage when the tertiary butyloxy carbonyl group is converted to a free carboxy group.

The aromatic group Ar is preferably a phenyl ring which is substituted by the groups M and -CONH-R. In such rings the group M is preferably in the 4-position relative to the group -CONH-R.

The amino acid or oligopeptide R-NH₂ is selected in order that the group R-NH of compounds of the present invention may be removed in vivo under the influence of an enzylene. Glutamic acid and aspartic acid are suitable amino acids, although other a-amino carboxylic acids may also be of use. The amino acids can be in the D or L configuration.

The production of compounds of the present invention requires the use of the amino acid or oligopeptide R-NH₂ as defined above. The t-butylated amino acid or oligopeptide may be prepared by conventional means. For example, glutamic acid may be reacted with t-butylacetate.

The amino acid or oliogopeptide with t-butyl protecting groups, R-NH₂, or acid addition salts thereof, e.g. R-NH₃⁺Cl⁻ may then be reacted with a compound of formula Z-Ar-COX where Ar is as defined above, X is hydroxy, a halide, e.g. chlorine, or another group that will allow the moiety -CO to form an amide linkage by techniques well known in the art of peptide chemistry, and Z is a group to be converted to the nitrogen mustard group M. The group Z is conveniently one which may be converted to an amine. The resulting amine may for example be a group -NH₂ or hydroxylyamine.

A preferred route of synthesis involves the reaction of the t-butylated amino acid or oliogopeptide, or their acid addition salts, e.g. di-t-butyl glutamate hydrochloride, with a compound of formula O₂N-Ar-COCl. The resulting intermediate XXII:

O₂N-Ar-CONH-R (XXII)

may then be converted to the nitrogen mustard group M.

This conversion may be performed by conventional methods, as described in our above mentioned co-pending International application. For example, the nitro group may first be converted to an amino group by hydrogenation, eg. by hydrogen in the presence of a Pd/C catalyst, to obtain the intermediate XXIII H₂N-Ar-CONH-R (XXIII)

The amine group may then be converted to the desired nitrogen mustard by appropriate substitution. For example, the amine group may be converted by reaction of the intermediate XXIII with ethylene oxide in a solvent, e.g. acetic acid, to produce the his (2-hydroxyethyl) amine derivative of XXIII, and then further reacting the derivative with a compound of the formula

A-SO₂-B where A is methyl, trifluoromethyl or tolyl and B is a halogen, (e.g. chlorine) in an organic solvent, e.g. pyridine, to obtain compounds according to the invention.

Following the production of the nitrogen mustard compounds of the invention by for example conversion of the intermediate XXII, the compounds may be purified by conventional means, e.g. chromatography and-/or crystallization.

Following the synthesis of the tertiary butyl ester compounds according to the invention, pro-drugs for use in the system described in our above mentioned co-pending International Application may be obtained.

According to a further embodiment of the invention, the nitrogen mustard compounds of the invention may be used to obtain nitrogen mustard pro-drugs of the formula:

M-Ar-CONH-R' where M and Ar are as defined above, and R'-NH is the residue of an α-amino acid R'-NH₂ or oligopeptide R'-NH₂. This is achieved by acid hydrolysis of compounds of the formula XX to remove the t-butyl protecting groups. Suitable acids include trifluoroacetic acid and formic acid in substantially non-aqueous form.

Removal of the tertiary butyl ester group can be carried out quite simply by maintaining the tertiary butyl ester in a substantially non-aqueous solution together with trifluoroacetic acid at room temperature, e.g. 15°-25° C. It is desirable to utilise an amount of trifluoroacetic acid that is at least equivalent to the tertiary butyl ester groups to be hydrolysed although the exact proportion of trifluoroacetic acid and the hydrolysis temperature are not critical, the use of lower temperatures and smaller proportions of trifluoroacetic acid serving merely to prolong the period of time necessary for total hydrolysis of the tertiary butyl ester group to take place.

We have found, in accordance with the present invention, that hydrolysis of the tertiary butyl ester group with trifluoracetic acid under non-aqueous conditions proceeds almost quantitatively (>80%) with degradation of the nitrogen mustard grouping under these reaction conditions being substantially completely avoided.

Formic acid can be used as an alternative to trifluoroacetic acid. However much more stringent reaction conditions are necessary. The temperature must be kept below that of room temperature, preferably at 10° C.; the concentration of ester must be low, preferably 5 mg/ml; the time of reaction must be extended, preferably to 48 hours. After this reaction period, the formic acid can be removed by lyophilisation. Under these conditions the deprotection proceeds to completion with a quantitative yield, and the resulting pro-drugs can be used Without further formulation.

The following Examples are given to illustrate the present invention. The following reaction scheme illustrates the production of three benzoic acid nitrogen mustard glutamate pro-drugs by hydrolysis of corresponding di-tertiary butyl esters:

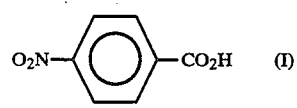    (I)

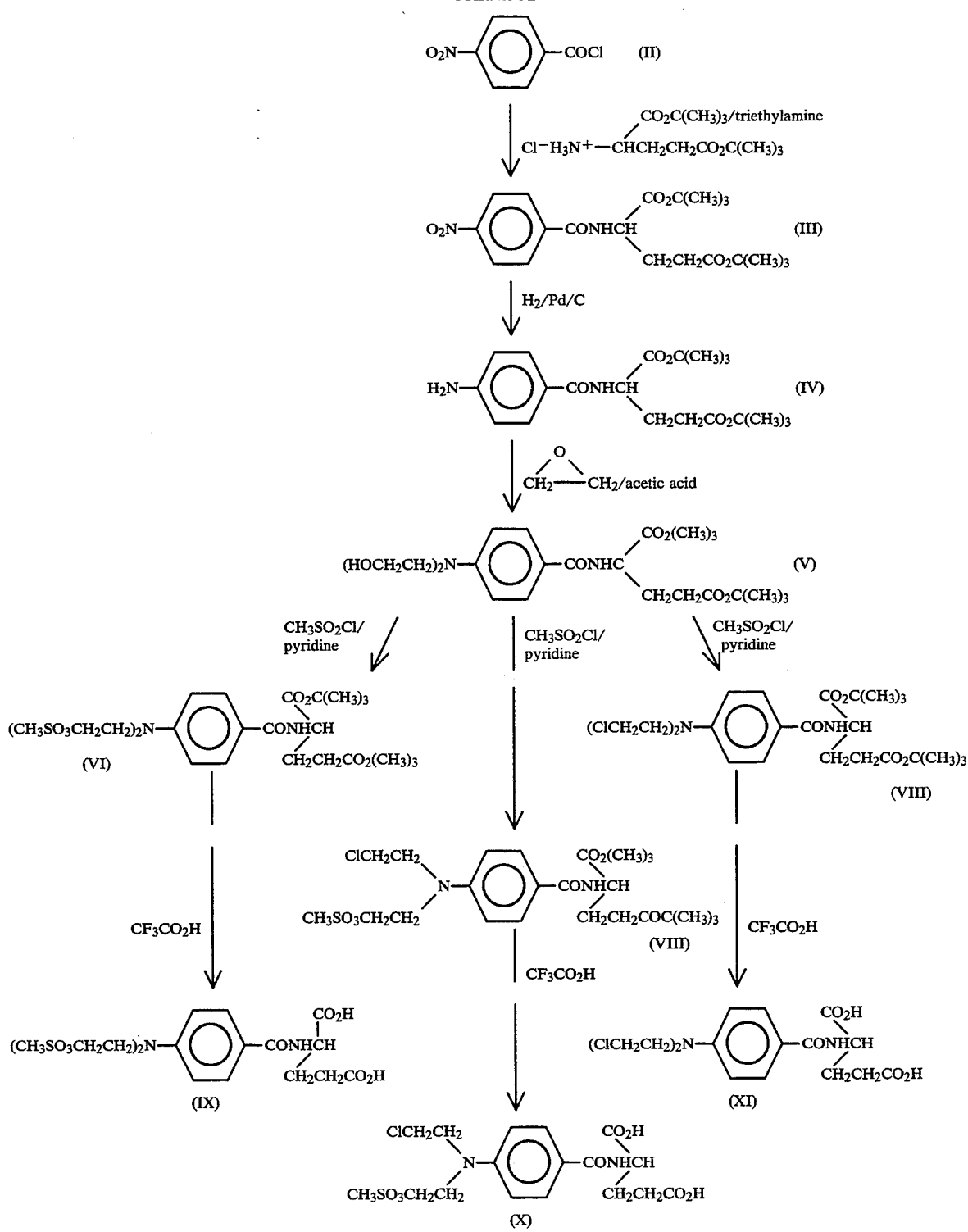

DITERTIARYBUTYLESTER = PROTECTING GROUPS

EXAMPLE 1

Experimental Section

Merck silica 60 (Art 7734, 9385, & 15111) were used in gravity columns. TLC was performed on precoated sheets of silica 60F$_{254}$ (Merck Art 5735). TLC spots were developed with Epstein spray.[1] Melting points were determined on a Kofler block (Reicheft Thermovar) melting point apparatus and are uncorrected. Electron impact spectra were determined with a VG 7070H spectrometer and a VG 2235 data system using the direct-insertion method, an ionizing voltage of 70 eV and trap current of 100 μA, and an ion-source temperature of 180°–200° C. FAB mass spectra were determined using xenon gas. Reported spectra are by electron impact unless otherwise stated. NMR spectra were determined in Me$_2$SO-d$_6$ on a Bruker AC250 (250 MHz) with Me$_4$Si as internal standard. Elemental analyses were determined by CHN Analysis Ltd., S. Wigston, Leicester, England.

Di-t-butyl 4-aminobenzoyl-L-glutamic acid (IV). Di-t-butyl 4-nitrobenzoyl-L-glutamic acid was prepared by a modification of the literature method.[2] To a solution of di-t-butyl L-glutamate hydrochloride (20 g, 68 mmol) in Et$_3$N (19 mL, 137 mmol) was added dropwise a solution of 4-nitrobenzoyl chloride (II) (13 g, 70 mmol) in CH$_2$Cl$_2$ (160 mL). Extractive workup gave a solid (III), hydrogenation of which gave the desired amine (IV). This was crystallised from EtOH-cyclohexane (45:55); yield - 85%.

Di-t-butyl 4-[bis(2-hydroxyethyl) amino]benzoyl-L-glutamate (V). The amine (IV) (21.97 g, 58 mmol) in HOAc (120 mL) was stirred with ethylene oxide (12 mL, 240 mmol) at room temperature for 48 h. The solvent was removed at 45° C. in vacuo and the residue partitioned between CH$_2$Cl$_2$ and H$_2$O. The organic phase was separated, washed with H$_2$O, dried (Na$_2$SO$_4$) and evaporated to dryness. The crude oil was chromatographed on silica gel (Merck, Art 9385) eluting with EtOAc-CH$_2$Cl$_2$ (1:1). The product (21.17 g, 78%) melted at 64°–65° C. NHR (Me$_2$SO-d$_6$) δ 1.38 (s, 9 H, t-Bu), 1.39 (s, 9 H, t-Bu), 1.97 (m, 2 H, CH$_2$CH$_2$CO$_2$t-Bu), 2.31 (t, 2 H, J =7.4 Hz, CH$_2$CH$_2$CO$_2$t-Bu), 3.51 (m, 8 H, 2HOCH$_2$CH$_2$), 4.29 (m, 1 H, CH), 4.80 (t, 2 H, J =4.8 Hz, 2HO), 6.69 (ABq, 2 H, J =8.9 Hz, arom. H-3, 5), 7.70 (ABq, 2 H, atom. H-2, 6), 8.15 (d, 1 H, J =7.6 Hz, NH); mass spectrum m/z 466 (M$^+$, 16%), 435 (M-HOCH$_2$, 65%), 208 (M-NHCH(CO$_2$t-Bu)CH$_2$CH$_2$CO$_2$t-Bu 100%). Anal. (C$_{24}$H$_{38}$N$_2$O$_7$.0.25H$_2$O) C, H, N (see Table 1).

Di-t-butyl 4-[bis(2-mesyloxyethyl)amino]benzoyl-L-glutamate (VI).

Di-t-butyl 4-[(2-chloroethyl)(2-mesyloxyethyl)amino]benzoyl-L-glutamate (VII)

Di-t-butyl 4-[bis(2-chloroethyl)amino]benzoyl-L-glutamate (VIII). A solution of (V) (2.00 g, 4.29 mmol) in pyridine (9.5 mL) was stirred with methanesulphonyl chloride (1.3 mL, 17.2 mmol) at 2° C. for 20 rain, followed by 50° C. for 10 min. The reaction mixture was partitioned between CH$_2$Cl$_2$ and H$_2$O. The organic phase was separated, washed with H$_2$O, dried (Na$_2$SO$_4$) and evaporated to dryness. The concentrate contained three reaction products each of which gave a positive result (blue colour) with the Epstein reagent. The mixture was chromatographed on silica gel (Merck, Art 15111) eluting with EtOAc-CH$_2$Cl$_2$ (1:9). The slowest eluting was the bis(2-mesyloxyethyl) derivative (VI) (0.6 g, 22%): mp 114°–116° C.; NMR (Me$_2$SO-d$_6$) δ 1.39 (s, 9 H, t-Bu), 1.40 (s, 9 H, t-Bu), 1.97 (m, 2 H, CH$_2$CH$_2$CO$_2$t-Bu) 2.32 (t, 2 H, J=7.4 Hz, CH$_2$CH$_2$CO$_2$t-Bu), 3.16 (s, 6 H, 2CH$_3$SO$_3$), 3.81 (t, 4 H, J =5.5 Hz, 2CH$_3$SO$_3$CH$_2$CH$_2$), 4.34 (m, 5 H, 2CH$_3$SO$_3$CH$_2$CH$_2$ and CH) 6.84 (ABq, 2 H, J=8.9 Hz, arom. H-3,5), 7.72 (ABq, 2 H, arom. H-2, 6), 8.27 (d, 1 H, J =7.7 Hz, NH); mass spectrum (FAB) m/z 623 ([M+H$^+$], 19%) 513 (M-CH$_3$SO$_3$CH$_2$, 10%) 364 (M-NHCH (CO$_2$t-Bu) CH$_2$CH$_2$CO$_2$t-Bu 100%). Anal. (C$_{26}$H$_{42}$N$_2$O$_{11}$S$_2$) C, H, N, S (see Table 1).

Eluting second was the (2-chloroethyl) (2-mesyloxyethyl) derivative (VII) (0.2 g, 8%): mp 71°–73° C.; NMR (Me$_2$SO-d$_6$) δ 1.39 (s, 9 H, t-Bu), 1.40 (s, 9 H, t-Bu), 2.00 (m, 2 H, CH$_2$CH$_2$CO$_2$t-Bu), 2.31 (t, 2 H, J =7.3 Hz, CH$_2$CH$_2$CO$_2$t-Bu), 3.15 (s, 3 H, CH$_3$SO$_3$), 3.77 (s, 4 H, ClCH$_2$CH$_2$), 3.82 (t, 2 H, J =5.5 Hz, CH$_3$SO$_3$CH$_2$CH$_2$), 4.33 (m, 3 H, CH$_3$SO$_3$CH$_2$CH$_2$ and CH), 6.82 (ABq, 2 H, J =8.9 Hz, arom. H-3, 5), 7.77 (ABq, 2 H, arom. H-2, 6), 8.24 (d, 1 H, J =7.6 Hz, NH); mass spectrum m/z 562 (M+100%) 453 (M-CH$_3$SO$_3$CH$_2$, 9%) 304 (M-NHCH (CO$_2$t-BU) CH$_2$CH$_2$CO$_2$t-Bu) 17%). Anal. (C$_{25}$H$_{39}$N$_2$OSCl S) C, H, N, Cl, S. (see Table 1).

The fastest eluting, his (2-chloroethyl) derivative (VIII) was present in such low yield (0.01 g, 0.4%) that a different procedure for production was followed. A solution of (V) (2.53 g, 5.43 mmol) was treated with methanesulphonyl chloride (1.7 mL, 22.5 mmol) in pyridine (13 mL) at 2° C. for 20 min, followed by 80° C. for 80 min. The mixture was partitioned as before, dried and concentrated to give two products which gave a positive result (blue colour) with the Epstein spray. The mixture was chromatographed on silica gel (Merck, 7734) and eluted in solvents as before. The slower eluting (2-chloroethyl) (2-mesyloxyethyl) derivative (VII) was present in very low yield, (0.01 g, 0.3%). Eluting faster was the bis(2-chloroethyl) derivative (VIII) (2.11 g, 77%): mp 142°–143° C.; NMR (Me$_2$SO-d$_6$) δ 1.39 (s, 9 H, t-Bu), 1.40 (s, 9 H, t-Bu), 1.99 (m, 2 H, CH$_2$CH$_2$CO$_2$t-Bu), 2.31 (t, 2 H, J =7.4 Hz, CH$_2$CH$_2$CO$_2$t-Bu) 3.78 (t, 8 H, J =5.0 Hz, 2ClCH$_2$CH$_2$), 4.34 (m, 1H, CH) 6.70 (ABq, 2 H, J =9.0 Hz, arom. H-3, 5), 7.77 (ABq, 2 H, arom. H-2, 6), 8.26 (d, 1 H, J=7.6 Hz, NH) mass spectrum m/z 502 (M$^+$, 4%), 453 (M-ClCH$_2$ 4%), 244 (M-NHCH(CO$_2$t-Bu)CH$_2$CH$_2$CO$_2$t-Bu, 100%). Anal. (C$_{24}$H$_{36}$N$_2$O$_5$Cl$_2$) C, H, N, Cl (see Table 1). Preparation of Diacids - General Method. Compounds (VI) (0.213 g), (VII) (0.127 g) or (VIII) (0.402 g) were suspended in TFA (1–2% w/v) and stirred for 30 min at room temperature. The acid was removed under reduced pressure at 30°–35° C. The remaining oil was diluted with ethyl acetate (1 mL) which was evaporated at the same temperature. This-dilution/evaporation step was repeated a further 19 times. Compound (IX) (0.19 g, 83%), 4-8 bis(2-mesyloxyethyl)amino]benzoyl-L-glutamic acid, was obtained as a pure product from (VI): NMR (Me$_2$SO-d$_6$) δ 1.99 (m, 2 H, CH$_2$CH$_2$CO$_2$H), 2.34 (t, 2 H, J =7.4 Hz, CH$_2$CH$_2$CO$_2$H), 3.16 (s, 6 H, 2CH$_3$SO$_3$), 3.81 (t, 4 H, J =5.4 Hz, 2CH$_3$SO$_3$CH$_2$CH$_2$), 4.33 (m, 5 H, 2CH$_3$SO$_3$CH$_2$CH$_2$ and CH), 6.84 (ABq, 2 H, J =8.9 Hz, arom. H-3.5), 7.75 (ABq, 2 H, arom. H-2, 6), 8.29 (d, 1 H, J =7.7 Hz, NH). The presence of EtOAc, noted in the elemental analysis, was confirmed by NMR; mass spectrum (FAB) m/z 511 ([M+H$^+$], 20%), 364 (M-NHCH(CO$_2$H)CH$_2$CH$_2$CO$_2$H, 100%). Anal. (C$_{18}$H$_{26}$N$_2$O$_{11}$S$_2$.1.1 TFA.0.45 EtOAc) C, H, N, S, F (see Table 1). This compound reacted positively (blue colour) with the Epstein spray reagent.

Compound (X) (0.09 g, 82%), 4-[(2-chloroethyl) (2-mesyloxyethyl)amino]benzoyl-L-glutamic acid, was similarly obtained from (VII): NMR (Me$_2$SO-d$_6$) δ 1.99 (m, 2 H, CH$_2$CH$_2$CO$_2$H), 2.33 (t, 2 H, J =7.3 Hz, CH$_2$CH$_2$CO$_2$H), 3.16 (s, 3 H, CH$_3$SO$_3$), 3.77 (s, 4 H, ClCH$_2$CH$_2$), 3.83 (t, 2 H, J =5.7 Hz, CH$_3$SO$_3$CH$_2$CH$_2$), 4.33 (m, 3 H, CH$_3$SO$_3$CH$_2$CH$_2$ and CH), 6.82 (ABq, 2 H, J =9.0 Hz, atom. H-3, 5), 7.77 (ABq, 2 H, arom. H-2, 6), 8.29 (d, 1 H, J =7.7 Hz, NH); mass spectrum (FAB) m/z 451 ([M+H$^+$], 5%), 401 (M-ClCH$_2$, 4%), 341 (M-CH$_3$SO$_3$CH$_2$, 17%). Anal. (C$_{17}$H$_{23}$N$_2$O$_8$ClS·0.25 TFA) C, H, N, Cl, F, S (see Table 1). This compound reacted positively (blue colour) with the Epstein spray reagent.

Compound (XI) (0.33 g, 94%), 4-[bis(2-chloroethyl-)amino]benzoyl-L-glutamic acid was likewise obtained from (VIII): NMR (Me$_2$SO-d$_6$) δ 2.00 (m, 2 H, CH$_2$CH$_2$CO$_2$H), 2.34 (t, 2 H, J =7.4 Hz, CH$_2$CH$_2$CO$_2$H), 3.78 (t, 8 H J =5.2 Hz, 2ClCH$_2$CH$_2$), 4.34 (m, 1H, CH), 6.80 (ABq, 2 H, J =9.0 Hz, arom. H-3, 5), 7.77 (ABq, 2 H, arom. H-2, 6), 8.29 (d, 1 H, J =7.8 Hz, NH): mass spectrum m/z 372 (M-H$_2$O, 12%), 244 (M-NHCH(CO$_2$H)CH$_2$CH$_2$CO$_2$H, 45%). Anal. (C$_{16}$H$_2$ON$_2$O$_5$Cl$_2$.0.4 TFA) C, H, N, Cl, F (see Table 1). This compound reacted positively (blue colour) with the Epstein spray reagent.

EXAMPLE 2

The di-t-butyl ester VII (3.00 g 5.33 mmol) produced in Example 1 is stirred in formic acid (98%, 600 ml) at 10° C. for 48 h. It is then transferred into vials and frozen in liquid nitrogen, prior to lyophilisation on a freeze dryer. When all the acid has been removed, the vials are capped while still under vacuum on the freeze dryer. The deprotection is quantitative and gives the dicarboxylate X as a white powder as final product (2.40 g, 100%)

NMR. (Me$_2$SO-d$_6$) δ 1.98 (m,2H, CH$_2$CH$_2$CO$_2$H), 2.34 (t, 2H, J=7.3 Hz, CH$_2$CH$_2$CO$_2$H), 3.16 (s,3H, CH$_3$SO$_3$), 3.77 (s, 4H, ClCH$_2$CH$_2$), 3.83 (t, 2H, J =5.4 Hz, CH$_3$SO$_3$CH$_2$CH$_2$), 4.33 (m,3H, CH$_3$SO$_3$CH$_2$CH$_2$& CH), 6.82 (ABq, 2H, J =8.9 Hz, arom H-3,5), 7.77 (ABq, 2H, arom H-2,6), 8.27 (d, 1H, J =7.8 Hz, NH)

mass spectrum FAB m/z 451([M+H$^+$], 17%), 401(M-ClCH$_2$,7%), 304(M-NHCH(CO$_2$H)CH$_2$CH$_2$CO$_2$H, 100%) Anal. C$_{17}$H$_{23}$N$_2$O$_8$ClS.0.2H$_2$O)

| Expected | Found |
|---|---|
| C 44.92 | 44.89 |
| H 5.19 | 5.41 |
| N 6.17 | 5.78 |
| Cl 7.79 | 7.83 |
| S 7.05 | 6.97 |

References (1) Epstein, J.; Rosenthal, R. W.; Ess, R. J. Anal. Chem., 1955, 27, 1435.

(2) Hynes, J. B.; Yang, Y. C. S.; McCue, G. H.; Benjamin, M. B. In "Folyl and Antifolyl polyglutamates" Eds. Goldman, I. D.; Chabner, B. A.; Bertino, J. R. Plenum Press, N.Y. 1983, 101.

I claim:

1. A process for the preparation of a compound of the formula XX:

M-Ar-CONH-R (XX)

wherein Ar represents a phenylene group which may be substituted, R-NH represents a group which is a residue of an α-amino acid R-NH$_2$ or oliogopeptide R-NH$_2$ and contains at least one carboxylic acid group in the form of a tertiary butyl ester, and M represents a nitrogen mustard group of formula

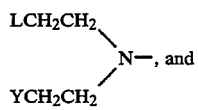

wherein Y and L, which may be the same or different, are leaving groups selected from the group consisting of halogen, mesyloxy, trifluoromesyloxy and 4-tosyloxy, the process comprising:

reacting a compound of formula (HOCH$_2$CH$_2$)$_2$N-Ar-CONH-R wherein R-NH and Ar are defined above, with a compound of formula

A-SO$_2$-B wherein A is a methyl, trifluoromethyl or 4-tosyl group, and B is a halogen.

2. A process for the production of a pro-drug of formula

M-Ar-CONH-R' wherein M represents a nitrogen mustard group of formula

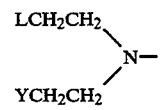

wherein Y and L, which may be the same or different, are leaving groups, Ar represents a phenylene group which may be substituted, and R'-NH represents a group which is residue of an α-amino acid R'-NH$_2$ or oligopeptide R'-NH$_2$, the process comprising:

TABLE 1

| COMPOUND | Elemental Analysis | | | | | | | | | | | |
|---|---|---|---|---|---|---|---|---|---|---|---|---|
| | CALCULATED | | | | | | FOUND | | | | | |
| | C | H | N | Cl | F | S | C | H | N | Cl | F | S |
| Di-t-butyl 4-[bis(2-hydroxyethyl)amino]benzoyl-L-glutamate 0.25 H$_2$O (V) | 61.19 | 6.13 | 5.95 | | | | 61.32 | 8.23 | 5.92 | | | |
| Di-t-butyl 4-[bis(2-mesyloxyethyl)amino]benzoyl-L-glutamate (VI) | 50.14 | 6.80 | 4.50 | | | 10.30 | 50.43 | 6.82 | 4.46 | | | 10.03 |
| Di-t-butyl 4-[(2-chloroethyl-2-mesyloxyethyl)amino]benzoyl-L-glutamate (VII) | 53.32 | 6.98 | 4.98 | 6.30 | | 5.69 | 53.05 | 6.96 | 4.91 | 6.14 | | 5.81 |
| Di-t-butyl 4-bis(2-chloroethyl)amino]benzoyl-L-glutamate (VIII) | 57.25 | 7.21 | 5.57 | 14.08 | | | 57.22 | 7.18 | 5.49 | 14.25 | | |
| 4-[bis(2-mesyloxyethyl)amino]benzoyl-L-glutamic acid 1.1 TEA 0.45 EtOAc (IX) | 39.11 | 4.58 | 4.15 | | 9.28 | 9.49 | 39.46 | 4.77 | 3.89 | | 9.05 | 9.20 |
| 4-[(2-chloroethyl)(2-mesyloxethyl)amino]benzoyl-L-glutamic acid 0.25 TFA (X) | 43.84 | 4.85 | 5.84 | 7.40 | 2.97 | 6.69 | 43.62 | 5.22 | 5.52 | 7.28 | 2.62 | 6.49 |
| 4-[bis-(2-chloroethyl)amino]benzoyl-L-glutamic acid 0.4 TFA (XI) | 46.19 | 4.70 | 6.41 | 16.23 | 5.22 | | 45.85 | 4.85 | 6.29 | 16.10 | 5.27 | | hydrolyzing, by acid hydrolysis using trifluroracetic acid or formic acid, a compound of the formula XX:

M-Ar-CONH-R (XX)

wherein Ar represents a phenylene group which may be substituted, R-NH represents a group which is a residue of an α-amino acid R-NH$_2$ or oliogopeptide R-NH$_2$ and contains at least one carboxylic acid group in the form of a tertiary butyl ester, and M represents a nitrogen mustard group of formula

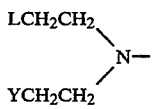

where Y and L, which may be the same or different, are leaving groups, to remove t-butyl protecting group(s).

3. The process according to claim 2, wherein the acid hydrolysis is performed using trifluoroacetic acid.

4. The process according to claim 2, wherein the acid hydrolysis is performed using formic acid.

5. The process according to claim 1, wherein Y and L, which may be the same or different, are selected from the group consisting of halogen, mesyloxy, trifluoromesyloxy, and 4-tosyloxy.

6. The process according to claim 1, wherein the group —M is in the 4-position relative to the group —CONH-R.

7. The process according to claim 1, wherein the α-amino acid R-NH$_2$ is selected from the group consisting of glutamic acid and aspartic acid.

8. The process according to claim 1, wherein the α-amino acid R-NH$_2$ is an L-amino acid.

9. The process according to claim 1, wherein the compound of formula (XX) is:

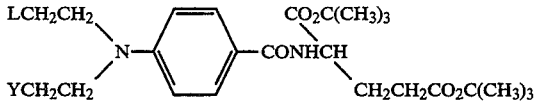

wherein Y and L, which may be the same or different, are chloro or mesyloxy groups.

* * * * *